US012694961B2

(12) United States Patent
Saunders

(10) Patent No.: US 12,694,961 B2
(45) Date of Patent: Jul. 28, 2026

(54) SYSTEM AND METHOD FOR SECURELY GIVING ELECTRONIC PRESCRIPTIONS DIRECTLY TO PATIENTS

(71) Applicant: Caleb Saunders, Roswell, NM (US)

(72) Inventor: Caleb Saunders, Roswell, NM (US)

(*) Notice: Subject to any disclaimer, the term of this patent is extended or adjusted under 35 U.S.C. 154(b) by 340 days.

(21) Appl. No.: 18/192,720

(22) Filed: Mar. 30, 2023

(65) Prior Publication Data

US 2023/0335245 A1    Oct. 19, 2023

Related U.S. Application Data

(60) Provisional application No. 63/331,462, filed on Apr. 15, 2022.

(51) Int. Cl.
G16H 20/10        (2018.01)
(52) U.S. Cl.
CPC ......... G16H 20/10 (2018.01); G06Q 2220/10 (2013.01)
(58) Field of Classification Search
CPC ........ G16H 20/10; G16H 40/67; G16H 40/20; G06Q 2220/10; G06F 21/6245; G06F 21/64; G06F 21/602
See application file for complete search history.

(56) References Cited

U.S. PATENT DOCUMENTS

| | | | | |
|---|---|---|---|---|
| 2019/0198144 A1* | 6/2019 | Blackley | ................ | G16H 20/10 |
| 2019/0362828 A1 | 11/2019 | Laxer | | |
| 2020/0005912 A1* | 1/2020 | Saliman | ................ | G16H 10/20 |
| 2020/0135317 A1* | 4/2020 | Karbowicz | ........... | G06Q 30/08 |
| 2020/0219601 A1 | 7/2020 | Blackley et al. | | |
| 2020/0286607 A1 | 9/2020 | Abuzeni | | |
| 2020/0294642 A1* | 9/2020 | Bostic | ................... | G16H 50/20 |
| 2020/0388365 A1 | 12/2020 | Ponceleon et al. | | |
| 2021/0005292 A1* | 1/2021 | McFarlane | ............. | G06F 16/27 |
| 2021/0005296 A1* | 1/2021 | McFarlane | ............. | G16H 10/60 |
| 2021/0005302 A1* | 1/2021 | McFarlane | ............. | G06Q 30/06 |
| 2021/0243028 A1* | 8/2021 | Song | .................... | H04L 9/3228 |
| 2021/0358605 A1 | 11/2021 | Lamoncha | | |
| 2021/0386964 A1* | 12/2021 | Youngblood | ........ | A47C 21/044 |
| 2022/0131699 A1* | 4/2022 | Kimmel | ............... | H04L 9/3231 |
| 2023/0317224 A1* | 10/2023 | Prajapati | ............. | G06Q 20/363 |
| | | | | 705/51 |
| 2024/0079104 A1* | 3/2024 | Maeda | ............... | G06Q 20/3678 |

OTHER PUBLICATIONS

Method and Apparatus for Blockchain Verification of Healthcare Prescriptions (Year: 2016).*
Systems and Methods for Prescription and Dosing of Therapeutic Stimuli Using Recorded Guarantees (Year: 2020).*
Medicine Supply Control (Year: 2022).*

(Continued)

*Primary Examiner* — John W Hayes
(74) *Attorney, Agent, or Firm* — Kameron W. Kramer

(57) ABSTRACT

The present invention provides a system and method for medical providers to give electronic prescriptions ("eRx") to patients. When an eRx is generated by a medical provider, a blockchain is initiated that stores all the information of the eRx. This eRx is given to the patient on their digital storage device. The eRx can be provided to a permissioned peer, such as a pharmacy, whereby the permissioned peer is able to confirm the authenticity of the eRx.

6 Claims, 2 Drawing Sheets

(56) References Cited

OTHER PUBLICATIONS

A Drug Dispensing Method, Block Chaining Node Device And System (Year: 2018).*

The Working Method Of A Medical Prescription Based On Blockchain Of Valid Configuration (Year: 2019).*

Benita et al, "Authentic Drug Usage and Tracking with Blockchain Using Mobile Apps", International Journal of Interactive Mobile Technologies, vol. 14, No. 17, 2020 (Year: 2020).*

Holbl et al., "A Systematic Review of the Use of Blockchain in Healthcare", Faculty of Electrical Engineering and Computer Science, University of Maribor, Maribor Slovenia, Symmetry 2018, 10, 470 (Year: 2018).*

Shruthi et al, "Blockchain and its Applications in Healthcare data: A Survey", Siddaganga Institute of Technology, Tumkur, India, Grenze International Journal of Engineering and Technology, July Issue, 2021 (Year: 2021).*

Bhargave, Richard, "Blockchain Technology and Its Application: A Review", The IUP Journal of Information Technology, vol. XV, No. 1, 2019 (Year: 2019).*

Farzana, et al, "Symmetric Key-Based Patient Controlled Secured Electronic Health Record Management Protocol", Department of Computer Science and Engineering, United International University, Bangladesh, Journal of High Speed Networks, 25, 2019 (Year: 2019).*

* cited by examiner

SYSTEM AND METHOD FOR SECURELY GIVING ELECTRONIC PRESCRIPTIONS DIRECTLY TO PATIENTS

CROSS-REFERENCE TO RELATED APPLICATIONS

This application claims the benefit of U.S. Provisional Patent Application Ser. No. 63/331,462 filed Apr. 15, 2022, titled "System and Method for Securely Giving Electronic Prescriptions Directly to Patients," and the subject matter thereof is incorporated herein by reference thereto.

TECHNICAL FIELD

The present disclosure generally relates to the practice of medicine in the issuing of prescriptions, and specifically to using blockchain technology for storing and transferring electronic prescriptions.

BACKGROUND OF THE INVENTION

For a patient to receive a medication from a pharmacy they need a prescription written by a suitably licensed provider. Historically these prescriptions were written on paper and given to the patient after being evaluated by the provider and prior to the patient leaving the institution.

In order to decrease transcription errors and make forging prescriptions harder most medical institutions have moved to sending prescriptions electronically to the patient's pharmacy of choice. Though this method of prescribing has increased security and decreased transcription errors, it has also ushered in a new suite of errors.

Sometimes the prescriptions go "missing" between the medical institution and the pharmacy. This leaves the patient in a position where they are calling between the pharmacy and the institution trying to figure out how to obtain their medication. Also, current law mandates that if the medication is a controlled substance then the prescription cannot be transferred until, if it's only schedule III-V, one fill has been filled at the current pharmacy. If the pharmacy does not have the medication, then the provider must send in a new prescription to another pharmacy and thus duplicate the prescription. There have also been times where a prescription is sent to a pharmacy that is closed and the patient cannot obtain their prescribed medication until a day or two later (which can be detrimental in cases where the medication is an antibiotic or antiepileptic).

Various systems and methods have been developed and are present in the prior art that try and solve some of these issues, although many issues still remain. US 20210358605 A1 discloses a database for all patient prescriptions, but it does not give to patient directly.

US 20200388365 A1 discloses decentralized prescription refills, but it does not give to patient directly.

US 20200286607 A1 discloses prescription data verification, but again it does not give the prescription data to the patient, but only an "embedded prescription code". This does not afford the patient the additional safety features of having a record of the actual prescription on their personal computing device. This also requires pharmacies to share their drug pricing and availability, which many pharmacies are not willing to do for competitive reasons.

US 20200219601 A1 discloses an enhanced prescription management system which provides more pricing and drug availability than giving the prescription to the patient.

US 20200135317 A1 discloses methods and systems for patient control of an electronic prescription. This invention uses a third-party system that the patient has access to for managing their electronic prescriptions. By never fully transferring ownership of the prescription to the filling pharmacy it introduces inefficiencies into the system. "Thus, the methods and systems of the present disclosure may allow a patient device to direct a refill of the prescription to be filled at a first pharmacy once an electronic prescription is uploaded to a patient wallet. The patient device may select a second pharmacy to refill the prescription (e.g., for a subsequent prescription refill) without transferring the prescription from the first pharmacy that filled the prescription previously. In this way, the patient device may not contact the first pharmacy during subsequent refills of the prescription." There is the potential for duplication of the prescription and pharmacies may not want to interact with such a system. The electronic prescription wallet relies on a central service, which can mean a single point of failure, rather than a distributed network of permissioned nodes.

US20190362828 A1 discloses systems and methods for electronic prescriptions. This requires pharmacies to "bid" on prescriptions and share costs/prices, which most pharmacies are not willing to do.

The present invention proposes a system whereby prescriptions can move to a blockchain based technology to provide a solution to the problems that arise in the prior art. Blockchain technology provides a way to allow the patient to leave the medical institution with a prescription, as the patient used to do with hard copy prescriptions, while also supplying the security and safety of electronic prescriptions by giving the prescriptions to the patient on the patient's digital storage devices.

None of the prior art fully addresses the problems resolved by the present invention. The present invention overcomes these limitations contained in the prior art by providing a system that is reliable, safe, effective, easy to use, and provides many benefits that are lacking in the prior art.

Certain embodiments of the invention have other steps or elements in addition to or in place of those mentioned above. The steps or element will become apparent to those skilled in the art from a reading of the following detailed description when taken with reference to the accompanying figures, if any.

SUMMARY OF THE INVENTION

The present invention provides a method for medical providers to give electronic prescriptions ("eRx") to patients, comprising an eRx for a patient is generated by a medical provider, wherein a genesis block that contains the information of the eRx is generated and initiates a new transactional chain by the medical provider for each new prescription, wherein the blockchain of the eRx is stored on one or more digital storage devices, wherein each transaction of the blockchain of the eRx contains a hash generated using nonce data that is only possessed by Permissioned Peers (as defined herein), wherein the one or more servers is accessible by Permissioned Peers, wherein the one or more servers provide all Permissioned Peers with timestamped, nonce data, and wherein the blockchain of the eRx without the nonce is given to the patient on a digital storage device. The method for generating and transferring an eRx further comprising a patient providing the eRx on the digital storage devices without the nonce to a Permissioned Peer, wherein the Permissioned Peer confirms the authenticity of the eRx by supplying the nonce data from one or more servers to verify the hash of the blockchain of the eRx, wherein the one or more servers verifies the Permissioned Peer, and wherein if the Permissioned Peer is verified by the one or more servers, a new block is added to the blockchain of the eRx and the Permissioned Peer is able to access the eRx.

The present invention further provides a method for tracking all refill events of an eRx, wherein each refill, once dispensed to the patient, will push a new block to the eRx blockchain. The new block that is added to the blockchain of the eRx contains the updated information for the filled prescription.

The present invention further provides a method for refilling an eRx, comprising an eRx for a patient is generated by a medical provider, wherein a genesis block that contains the information of the eRx is generated and added to a blockchain by the medical provider, wherein the blockchain of the eRx is stored on one or more servers, wherein the blockchain of the eRx contains a hash generated using nonce data that is only possessed by Permissioned Peers, wherein the one or more servers is accessible by Permissioned Peers, wherein the one or more servers provide all Permissioned Peers with timestamped, nonce data, wherein the blockchain of the eRx without the nonce is given to the patient on a digital storage devices; and the eRx without the nonce is provided to a pharmacy by the patient, wherein the pharmacy is a Permissioned Peer, wherein the pharmacy confirms the authenticity of the eRx by supplying the nonce to verify the hash of the blockchain of the eRx, wherein the one or more servers verifies the pharmacy before a new block is added to the blockchain of the eRx, and wherein the pharmacy can fill the desired eRx.

The present invention further provides a method for transferring an eRx, comprising a patient requests to transfer a prescription from the pharmacy that is a Permissioned Peer; the pharmacy processes, requests, and generates the next block on the eRx blockchain to transfer eRx ownership to the patient, wherein the eRx is transferred back to the patient's digital storage devices; the patient takes the eRx to a new pharmacy; the new pharmacy generates a new block and pushes to the eRx blockchain once validity of the eRx has been verified and ownership of eRx has been accepted; and the new block is added to the blockchain and pushed to the pharmacy.

DETAILED DESCRIPTION OF THE INVENTION

Figure 1:
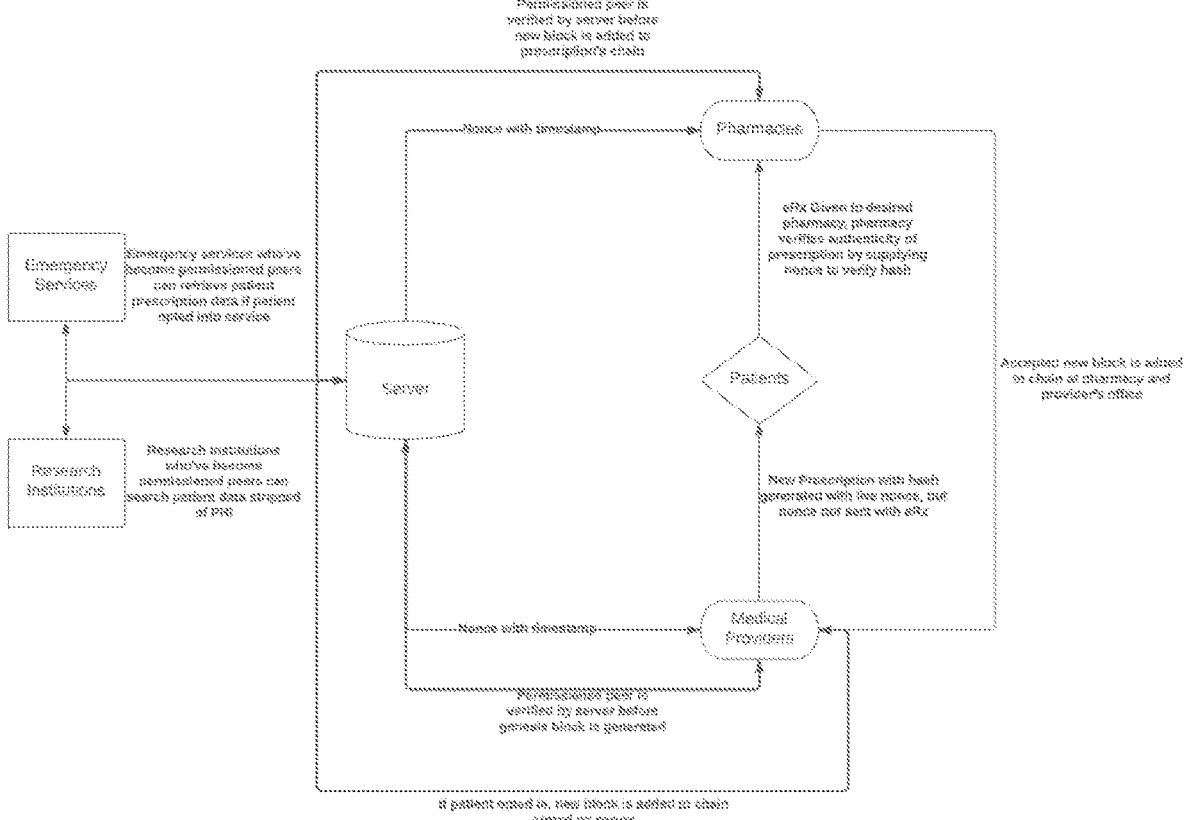
FIG. 1 illustrates a flow diagram of the present invention.

The best mode for carrying out the invention will be described herein. The following embodiments are described in sufficient detail to enable those skilled in the art to make and use the invention. It is to be understood that other embodiments would be evident based on the present disclosure, and that system, process, or mechanical changes may be made without departing from the scope of the present invention.

In the following description, numerous specific details are given to provide a thorough understanding of the invention. However, it will be apparent that the invention may be practiced without these specific details. To avoid obscuring the present invention, some well-known system configurations, and process steps are not disclosed in detail. The figures illustrating embodiments of the system, if any, are semi-diagrammatic and not to scale and, particularly, some of the dimensions are for the clarity of presentation and are shown exaggerated in the drawing figures.

Alternate embodiments have been included throughout, and the order of such are not intended to have any other significance or provide limitations for the present invention.

The present invention provides a system and methods utilizing blockchain technology for securely generating and giving an electronic prescription (the "eRx") directly to a patient, refilling an eRx, and transferring an eRx to a different pharmacy.

The problem with simply adopting a blockchain approach is that the security of a cryptocurrency is enforced by the length of the chain. The longer the chain, the harder it is to forge a block. To ensure security, the present invention provides a network of permissioned peers and a third-party server(s). The third-party server(s) keeps a list of all permissioned parties, such as medical providers, research institutes, pharmacies, etc. (each a "Permissioned Peer", and collectively the "Permissioned Peers"). Patients choose which Permissioned Peers they want to share their eRx with. Only blocks generated by Permissioned Peers are accepted as authentic. The third-party server(s) also provides random data, in cryptography it's called "nonce", used to hash each transaction/block of the blockchain. Each nonce data is assigned an active timeframe, whereby it is added to each eRx transaction prior to hashing the eRx and used for generating a unique hash (may also be referred to as a digest) for each transaction/block. In traditional blockchain technology for currency, all members get information about each transaction, whereas in the network of the present invention only Permissioned Peers chosen by the patient receive transactional data for the given eRx.

Active refills remaining on a prescription currently can be transferred from one pharmacy to another. This can require substantial amounts of time by the pharmacies involved and has the potential for transcription errors when the pharmacies verbally transfer the prescriptions. With a blockchain ledger of transactions an eRx with active refills can be requested back by the patient, be given back to the patient by the pharmacy, and then the patient can take it on their digital storage devices wherever they desire while maintaining the security and safety of the eRx.

By giving the patient the eRx there are additional safety measures in place. The patient has a record of every eRx they have ever had, moving forward once this solution was implemented, and thus would take with them their entire record wherever they went.

When giving ownership of a patient's current eRx to a pharmacy they are still able to see the record of their eRx on their computing device. Thus, any eRx may be double-checked by a patient at the time of pick-up. With hard copy prescriptions the patient gives the prescription to the pharmacy. Thus, there is no way for the patient to validate that the prescription was correctly filled by the pharmacy unless they call their medical institution and verify with them. Having a record of the eRx on the patient's computing device allows the patient to directly compare the end product from the pharmacy with the eRx they gave to the pharmacy.

Another safety mechanism that is implemented with the present invention is the ability to load images into the patient's eRx record. Every medication has a national drug code ("NDC"), and most are imaged. Once an eRx is filled at the pharmacy the image of the NDC used to fill the prescription could be sent to the patient's computing device so that they could verify that the medication they received looks the same as that verified by the pharmacy.

Multiple safety measures are provided that are not currently in place by giving the patient a record of an eRx and being able to update that record in real-time with an image of the correct medication. Every patient could take a bottle of pills from the pharmacy and compare the medication name, strength, directions, and pill image to that on their computing device and ensure no mistakes were made by the pharmacy. These safety measures could save lives.

Text-to-speech has also become commonplace technology on most computing devices. An eRx record on a patient's own computing device would afford an illiterate patient the ability to have their eRx directions read to them utilizing text-to-speech technology.

FIG. 1 illustrates a flow diagram of the present invention showing the process of prescribing of a new eRx. The first block of a blockchain is a genesis block. When a medical provider generates a new eRx, a new blockchain is initiated as the genesis block. All subsequent transactions are added to the blockchain of that eRx on the digital storage devices of the originating provider, patient, and Permissioned Peers chosen by the patient. Simply put, a prescription blockchain of an eRx is a secure, digital transactional record of all events concerning the given prescription. A patient may elect to share their prescription data with other parties as they see fit.

Digital storage devices, also referred to as personal computing devices, are any devices that allows a user to store their eRx.

To ensure security, the present invention provides a network of Permissioned Peers and a third-party server(s). The third-party server(s) are always available and accessible.

The third-party server(s) keeps a list of all Permissioned Peers, such as medical providers, research institutes, pharmacies, etc. Permissioned Peers can be verified using such national databases as the National Provider Identifier ("NPI"). Only Permissioned Peers are able to perform transactions, and hence add to the blockchain, of a particular blockchain.

The blockchain of the eRx is stored solely on the originating provider's, patient's, and any other Permissioned Peer's digital storage device chosen by the patient, unless the patient actively chooses to share their prescription data contained in the eRx with other parties, wherein each transaction of the blockchain of the eRx contains a hash/digest generated using nonce data that is only possessed by Permissioned Peers.

The present invention provides that the third-party server(s) also generate and distribute to all Permissioned Peers a random or semi-random number (the "nonce") for addition to any eRx transaction prior to the eRx data being processed through a hashing function. Each nonce would be specified as being valid for a set range of time only. The resulting hash is verified by any Permissioned Peer by supplying the nonce data corresponding to the transaction time.

Hashing is a function that meets the encrypted demands needed to secure information by transforming and generating an input data of any length into a string of a fixed size. Data is inputted and the final transformation is called a hash (or a "digest").

Hashing takes data of any length and puts the data into a set length. The same hash can never be created using different inputs. Each eRx in the present invention contains certain information, including, but not limited to, patient name, pharmacy name, prescription information, prescription date, patient address or other identifying information, time stamp, etc. The items are all combined to create a transaction ID (the "TXID"). The TXID is a hash value that is used to identify and confirm a transaction has happened.

Only blocks generated by Permissioned Peers are accepted as authentic and added to the server. The eRx is generated by the medical provider along using the nonce from the third-party server(s) for generating the hash. The Permissioned Peer is verified by the server before the genesis block is generated. The genesis block can only be created by permissioned, licensed medical providers. The eRx may be shared with any Permissioned Peer that is participating with the blockchain network. The authenticity of the eRx can be validated by looking at the timestamp on the eRx and supplying the appropriate nonce when hashing the eRx. Other validation methods may be implemented to confirm the authenticity of the eRx.

The genesis block is the first block in a blockchain of the eRx, and it contains transactions that when combined produce a unique hash. When a subsequent block is created, all the data of the genesis block is added to the new block to create a new hash. The previous hash is always used to create a new block in the blockchain. This is repeated. Each block leads back to the previous block through its hash, forming a chain back to the genesis block. This creates an unbreakable dependency in the blockchain.

The infrastructure of the blockchain of the eRx is formed by nodes. A node is a device that participates in a blockchain network, such as a computer or digital storage device. Nodes broadcast and validate transactions. A node receives a transaction submitted by a user and broadcasts it to the rest of the network. In a traditional blockchain, each of the nodes in the network check the authenticity and validity of a given transaction. In the current invention, only the Permissioned Peers, which are nodes that have joined the network, selected by the patient, and including the originating provider, receive and validate blocks for a given blockchain.

The new eRx is given to the patient by the medical provider, without the nonce, on their digital storage devices. Transfer of the eRx would be possible over wireless internet (WiFi), short range electromagnetic transmissions, by physical linkage to the patient's digital storage devices, or by other methods used to transmit digital data. The nonce remains on the server as a way to verify the eRx by the pharmacy and/or medical provider. The eRx is given to the desired pharmacy by the patient, though the eRx could still be sent directly by the medical provider to the pharmacy on the patient's behalf should the patient request it, and the pharmacy verifies authenticity of the eRx by supplying the nonce to verify the hash of each eRx.

The server(s) sends out timestamps with nonce data to all Permissioned Peers that are participating with the blockchain network. Any Permissioned Peer's system would look at the timestamp of the eRx, obtain the nonce data for that time, add the nonce data to the information of the eRx, then process the data through the hashing function and see if the resulting hash is identical to the hash on the eRx. As long as the two match, then the eRx is legitimate.

Emergency services and research institutions who have become Permissioned Peers can, if the patient has elected to participate in these services, search patient and/or eRx data, and the data may or may not be stripped of personally identifiable information according to the will of the individual patient.

Figure 2:
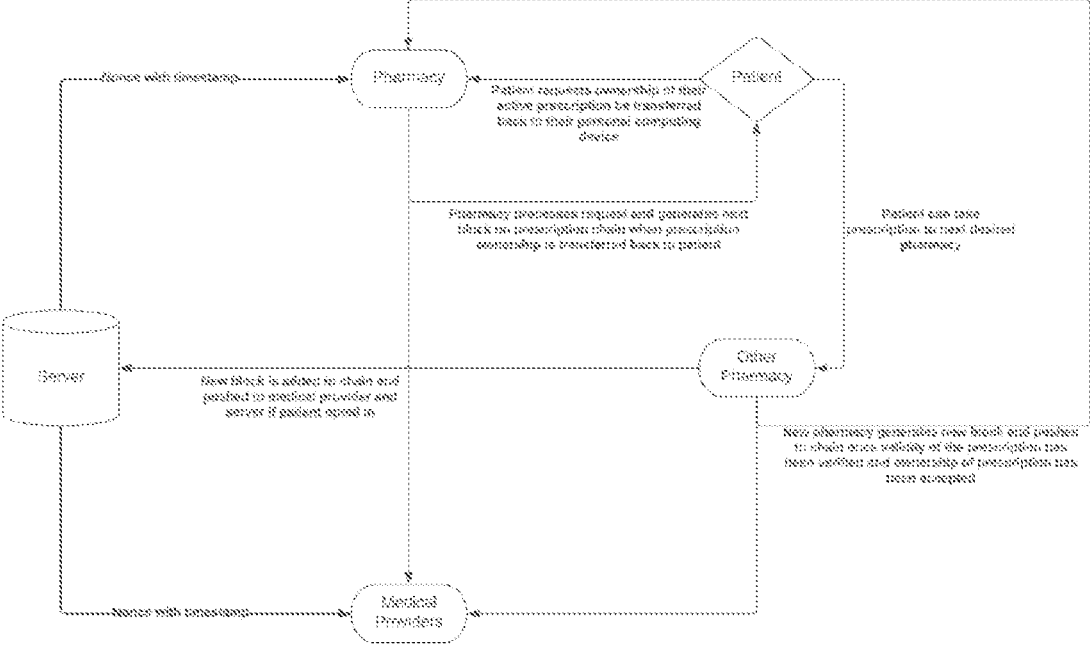
FIG. 2 illustrates a flow diagram of the present invention.

FIG. 2 illustrates a flow diagram of the present invention showing the process of a patient requesting ownership of an active eRx back from pharmacy in order to transfer to a new pharmacy. A patient requests ownership of an active eRx be transferred back to their digital storage devices from the pharmacy. The pharmacy then processes, requests, and generates the next block on the eRx chain when eRx ownership is transferred back to patient. A patient can then take the eRx to next desired pharmacy. The new pharmacy generates a new block and pushes to the eRx chain once validity of the eRx has been verified and ownership of eRx has been accepted. The new block is added to the chain and pushed to medical provider and pharmacy.

Each eRx has an "owner" category. There is only ever allowed one owner. The genesis block is owned by the generating provider. When the eRx is transferred to the patient the owner is now the patient. When the patient transfers the eRx to the pharmacy, then the pharmacy becomes the owner. This would be a new element to each eRx and would be tracked along with the eRx. Only the active owner of an eRx can choose to perform a transaction on the eRx (e.g., transfer the eRx, run a refill, etc.).

As soon as an eRx has been verified as legitimate by the receiving pharmacy, then that pharmacy would take ownership of the eRx and the new block on the chain would reflect that current status. Once a provider or pharmacy chooses to participate in the method of the present invention, they purchase/upgrade the software to interface with a blockchain network, or other method that allows the provider or pharmacy to interface with the blockchain network. At that point, they would become a Permissioned Peer.

The present invention allows active refills remaining on an eRx to be easily and securely transferred from one pharmacy to another. With a blockchain ledger of transactions an eRx with active refills may be requested back by the patient, given to the patient by the pharmacy, and then taken by the patient wherever they desire while maintaining the security and safety of an eRx.

After the genesis block, the second block is generated when the genesis block is given to the patient on their digital storage device. All subsequent blocks will be appended to the blockchain as the genesis block is processed. A key Permissioned Peer would be the original prescriber. Each new block that is created on the blockchain represents a new transaction and would be pushed back to the originating provider so the provider would know in real time whether the patient filled the medication and whether the patient has refills left on their eRx. The patient could opt-in to other data sharing, for example for use by emergency services, at their own discretion.

Security for cryptocurrency is a natural process by having multiple individuals working on a given blockchain and the chain length being so long that faking the chain is virtually impossible. In order to secure the eRx a server would be generating random data at random intervals that is sent to Permissioned Peers and included in the data for determining each eRx transaction hash; for this purpose, the random data will be termed "nonce". At any given time then there would be the "live" nonce that would be used for generating each eRx and transaction hash. The nonce would not be transmitted as part of the eRx payload but would be available to all Permissioned Peers in order to verify the authenticity of the eRx. When a patient gives the eRx to a pharmacy, the receiving pharmacy, being a Permissioned Peer, would supply the nonce for generating the hash and completing the transaction. Each transaction can then be verified by any Permissioned Peer.

To ensure all Permissioned Peers are using the same live nonce, the nonce is generated beforehand with a go-live timestamp, passed to all Permissioned Peers. This ensures that all Permissioned Peers transition to using the new live nonce simultaneously.

Another layer of security is derived by only accepting new transaction blocks if they originate from a Permissioned Peer. Every server node carries a list of Permissioned Peers and only accepts a transaction if it originated from a Peer on that list.

The patient may choose to also store their eRx data on a database in a Permissioned Peer's server, or keep the data between them, their medical provider, and their pharmacy. By choosing to share their eRx with a Permissioned Peer, access could be granted to certain emergency entities, e.g., emergency rooms to query the patient's prescriptions should the patient present to the entity in an incapacitated state. This would provide additional safety features but only if the patient opted into the program. A patient more concerned with keeping their personal health data private could choose to keep their eRx only on the Permissioned Peers of their provider(s), their digital storage devices, and/or their pharmacy(ies).

The same could also be done for research institutions. Personally identifiable information can be stripped from the eRx, at a patient's request, and access to the eRx can be given to research entities. This would also be an opt-in opportunity and would not be forced on any individual patient.

The present invention may also be utilized to transfer data other than prescription data by medical providers, including, but not limited to, medical information, financial data, etc. The present invention allows a user to transmit/transfer data from one party to a subsequent party, and the subsequent party is able to easily verify the authenticity of the data.

The best mode for carrying out the invention has been described herein. The previous embodiments are described in sufficient detail to enable those skilled in the art to make and use the invention. It is to be understood that other embodiments would be evident based on the present disclosure, and that system, process, or mechanical changes may be made without departing from the scope of the present invention.

In the previous description, numerous specific details and examples are given to provide a thorough understanding of the invention. However, it will be apparent that the invention may be practiced without these specific details and specific examples. While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters previously set forth herein or shown in the accompanying figures are to be interpreted in an illustrative and non-limiting sense.

What is claimed is:

1. A method for electronic prescriptions, comprising:
generating an electronic prescription for a patient;
generating a genesis block that contains information of the electronic prescription;
initiating a transactional chain for each new electronic prescription for the patient;
adding the genesis block to a blockchain of the electronic prescription,
wherein the transactional chain is associated with the blockchain of the electronic prescription;
storing the blockchain of the electronic prescription in one or more digital storage devices, wherein each transaction of the blockchain of the electronic prescription contains a hash generated using nonce data that is only possessed by permissioned peers, wherein the permissioned peers are medical providers that are chosen by the patient for sharing the electronic prescription, and wherein one or more servers is accessible by the permissioned peers providing, by the one or more servers, the nonce data that is timestamped to the permissioned peers;

providing, by the one or more servers, the blockchain of the electronic prescription without the nonce data to the patient on a digital storage device;

generating blocks by the permissioned peers, wherein the blocks are associated with new electronic prescriptions for the patient;

authenticating the generated blocks by participating peers of the permissioned peers using the nonce data; and adding the generated blocks that have been authenticated to the blockchain which is located in the one or more digital storage devices.

2. The method of claim 1, further comprising:

supplying, by a permissioned peer of the permissioned peers, the nonce data from the one or more servers to verify the hash of the blockchain of the electronic prescription;

confirming an authenticity of the electronic prescription by the permissioned peer based on the supply of the nonce data from the one or more servers;

verifying by the one or more servers the permissioned peer; and adding a new block to the blockchain of the electronic prescription based on the verification of the permissioned peer by the one or more servers; and accessing the electronic prescription by the permissioned peer.

3. The method of claim 1, further comprising: generating, by a permissioned peer of the permissioned peers, the nonce data; and correlating by the nonce data with a given time period.

4. The method of claim 1, wherein each subsequent block after the genesis block on the blockchain represents a new transaction and each subsequent block contains a timestamp and a corresponding hash using the associated nonce data.

5. The method of claim 4, wherein the new transaction is a subsequent change to the electronic prescription for the patient.

6. The method of claim 1, wherein the generated blocks added to the blockchain only contain certain information of the electronic prescription.

* * * * *